United States Patent

Clerc

[11] Patent Number: 5,856,439
[45] Date of Patent: Jan. 5, 1999

[54] FARNESYL TRANSFERASE INHIBITORS, PREPARATION THEREOF, AND PHARMACEUTICAL COMPOSITIONS CONTAINING SAME

[75] Inventor: Francois-Frédéric Clerc, Antony, France

[73] Assignee: Rhone-Poulenc Rorer S.A., Antony Cedex, France

[21] Appl. No.: 875,752

[22] PCT Filed: Feb. 7, 1996

[86] PCT No.: PCT/FR96/00198

§ 371 Date: Aug. 1, 1997

§ 102(e) Date: Aug. 1, 1997

[87] PCT Pub. No.: WO96/24611

PCT Pub. Date: Aug. 15, 1996

[30] Foreign Application Priority Data

Feb. 9, 1995 [FR] France .................................. 95/01489

[51] Int. Cl.⁶ .................................................. A61K 38/07
[52] U.S. Cl. .......................... 530/330; 530/329; 530/331; 514/18; 548/535; 562/557
[58] Field of Search ............................... 514/18; 530/331, 530/330, 329; 548/535; 562/557

[56] References Cited

FOREIGN PATENT DOCUMENTS

| | | |
|---|---|---|
| 0461869 | 12/1991 | European Pat. Off. . |
| 0523873 | 1/1993 | European Pat. Off. . |
| 0 618 221 | 10/1994 | European Pat. Off. . |
| WO 91/16340 | 10/1991 | WIPO . |
| WO 95/25092 | 9/1995 | WIPO . |
| 9624611 | 8/1996 | WIPO . |
| WO 96/24611 | 8/1996 | WIPO . |
| WO 96/24612 | 8/1996 | WIPO . |

*Primary Examiner*—Cecilia J. Tsang
*Assistant Examiner*—David Lukton
*Attorney, Agent, or Firm*—Raymond S. Parker, III; Michael B. Martin

[57] ABSTRACT

Novel farnesyl transferase inhibitors of general formula (I)

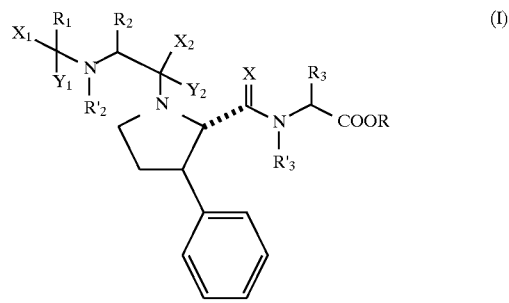

preparation thereof and pharmaceutical compositions containing same. In general formula (I), $R_1$ is $Y-S-A_1-$ (where Y is a hydrogen atom, an amino acid residue, a fatty acid residue, an alkyl or alkoxycarbonyl radical, or a radical $R_4-S-$, where $R_4$ is a $C_{1-6}$ alkyl radical optionally substituted by a phenyl radical, or a radical of general formula (II),

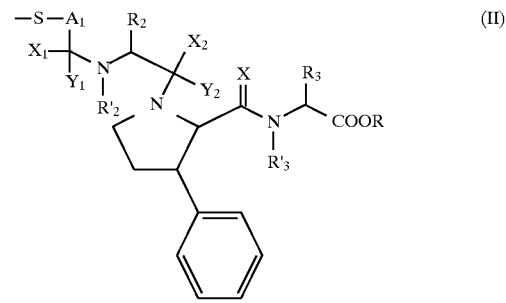

wherein $A_1$, $X_1$, $Y_1$, $R'_2$, $R'_2$, $X_2$, $Y_2$, $R_3$, $R'_3$ and R are as defined below, and $A_1$ is a $C_{1-4}$ alkylene radical optionally α-substituted in the $>C(X_1)(Y_1)$ grouping by an amino, alkylamino, alkanoylamino or alkoxycarbonylamino radical); $X_1$ and $Y_1$ are each a hydrogen atom or, taken together with the carbon atom to which they are attached, a $>C=O$ grouping; $R_2$ is a straight or branched $C_{1-4}$ alkyl radical optionally substituted by a cyclohexyl radical; $R'_2$ is hydrogen or alkyl; $X_2$ and $Y_2$ are each a hydrogen atom or, taken together with the carbon atom to which they are attached, a $>C=O$ grouping; $R_3$ is a $C_{1-4}$ alkyl radical optionally substituted by hydroxy, alkoxy, mercapto, alkylthio, alkylsulphinyl or alkylsulphonyl, with the proviso that, when $R_3$ is an alkyl radical substituted by a hyroxy, alkoxy, mercapto, alkylthio, alkylsulphinyl or alkylsulphonyl, with the proviso that, when $R_3$ is an alkyl radical substituted by a hydroxy radical, $R_3$ may form a lactone with the α-carboxy radical; $R'_3$ is hydrogen or alkyl; X is an oxygen or sulphur atom; and R is a hydrogen atom or an optionally substituted alkyl radical or an optionally substituted phenyl radical. These novel products have anti-cancer properties.

18 Claims, No Drawings

FARNESYL TRANSFERASE INHIBITORS, PREPARATION THEREOF, AND PHARMACEUTICAL COMPOSITIONS CONTAINING SAME

BACKGROUND OF THE INVENTION

The inhibition of farnesyl transferase, and consequently of the farnesylation of the ras protein, blocks the capacity of the mutated ras protein to transform normal cells into cancerous cells.

The C-terminal sequence of the ras gene contains the unit "CAAX" or "Cys-$Aaa_1$-$Aaa_2$-Xaa", in which Aaa represents an aliphatic amino acid and Xaa represents any amino acid.

It is known that tetrapeptides with a CAAX sequence can inhibit the farnesylation of the ras protein. For example, peptide inhibitors of farnesyl transferase, Cys-$Aaa_1$-$Aaa_2$-Xaa, which are more particularly represented by the peptides Cys-Val-Leu-Ser, Cys-Val-Ile-Met and Cys-Val-Val-Met which manifest their inhibitory activity at concentrations in the region of $10^{-6}M$ or $10^{-7}M$, have been described in PCT Application WO 91/16340 and in Application EP 0,461,869.

SUMMARY OF THE INVENTION

The present invention relates to the new farnesyl transferase inhibitors of formula:

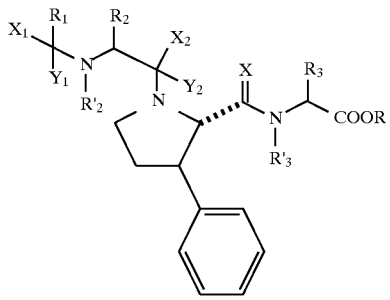

(I)

to their preparation and to the pharmaceutical compositions which contain them.

It has now been found, and this forms the subject of the present invention, that the peptides of general formula (I) manifest their inhibitory activity ($IC_{50}$) at concentrations of the order of $10^{-8}M$.

In the general formula (I), $R_1$, represents a radical of general formula Y—S—$A_1$— in which Y represents a hydrogen atom or an amino acid residue or a fatty acid residue or an alkyl or alkoxycarbonyl radical or an $R_4$—S— radical in which $R_4$ represents an alkyl radical containing 1 to 6 carbon atoms, optionally substituted by a phenyl radical, or a radical of general formula

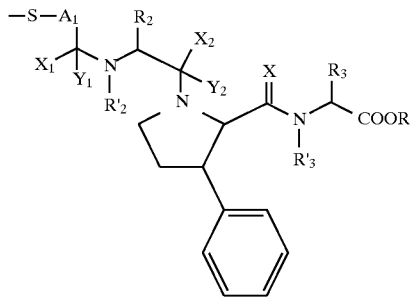

(II)

in which $A_1$, $X_1$, $Y_1$, $R_2$, $R'_2$, $X_2$, $Y_2$, X, $R_3$, $R'_3$ and R are defined as below, and $A_1$ represents a straight or branched alkylene radical containing 1 to 4 carbon atoms, optionally substituted at the position α to the >C($X_1$) ($Y_1$) group by an amino radical, an alkylamino radical containing 1 to 4 carbon atoms, an alkanoylamino radical containing 1 to 4 carbon atoms or an alkoxycarbonylamino radical in which the alkyl part contains 1 to 4 carbon atoms, $X_1$ and $Y_1$ each represent a hydrogen atom or form, together with the carbon atom to which they are bonded, a >C=O group, $R_2$ represents a straight or branched alkyl radical containing 1 to 4 carbon atoms, optionally substituted by a cyclohexyl radical, $R'_2$ represents a hydrogen atom or a straight or branched alkyl radical containing 1 to 6 carbon atoms, $X_2$ and $Y_2$ each represent a hydrogen atom or form, together with the carbon atom to which they are bonded, a >C=O group, $R_3$ represents a straight or branched containing alkyl radical containing 1 to 4 carbon atoms, optionally substituted by a hydroxyl radical, an alkoxy radical containing 1 to 4 carbon atoms, a mercapto radical, an alkylthio radical containing 1 to 4 carbon atoms, an alkylsulphinyl radical containing 1 to 4 carbon atoms or an alkylsulphonyl radical containing 1 to 4 carbon atoms, it being understood that, when $R_3$ represents an alkyl radical substituted by a hydroxyl radical, $R_3$ can form a lactone with the carboxyl radical at the α position, $R'_3$ represents a hydrogen atom or a straight or branched alkyl radical containing 1 to 6 carbon atoms, X represents an oxygen or sulphur atom, and R represents a hydrogen atom or an alkyl radical, optionally substituted by an alkoxy radical containing 1 to 4 carbon atoms, an alkylthio radical containing 1 to 4 carbon atoms, an alkylsulphinyl radical containing 1 to 4 carbon atoms, an alkylsulphonyl radical containing 1 to 4 carbon atoms, a phenyl radical, a phenoxy radical, a phenylthio radical, a phenylsulphinyl radical, a phenylsulphonyl radical, an alkylamino radical containing 1 to 4 carbon atoms or a dialkylamino radical in which each alkyl part contains 1 to 4 carbon atoms, or a phenyl radical, optionally substituted by one or a number of atoms or radicals, which are identical or different, chosen from halogen atoms and alkyl, alkoxy, alkylthio or alkanoyl radicals containing 1 to 4 carbon atoms.

More particular embodiments of the invention are compounds of formula I wherein $R_1$ represents a radical of formula Y—S—$A_1$— in which Y represents a hydrogen atom or a lysine residue or a fatty acid residue containing up to 20 carbon atoms and $A_1$ represents an ethylene or propylene radical optionally substituted by an amino radical, $X_1$ and $Y_1$ each represent a hydrogen atom or form, together with the carbon atom to which they are bonded, a >C=O group, $R_2$ represents an isopropyl, 1-methylpropyl, tert-butyl or cyclohexylmethyl radical, $R'_2$ represents a hydrogen atom or a methyl radical, $X_2$ and $Y_2$ each represent a hydrogen atom or form, together with the carbon atom to which they are bonded, a >C=O group, $R_3$ represents a methyl or ethyl radical substituted by a hydroxyl, methoxy, mercapto, methylthio, methylsulphinyl or methylsulphonyl radical, $R'_3$ represents a hydrogen atom or a methyl radical, X represents an oxygen atom, and R represents a hydrogen atom or an alkyl radical containing 1 to 4 carbon atoms, optionally substituted by an alkoxy radical, or a phenyl radical.

More particularly still, $R_1$ represents a radical of formula Y—S—$A_1$— in which Y represents a hydrogen atom and $A_1$ represents an ethylene or propylene radical optionally substituted by an amino radical, $X_1$ and $Y_1$ each represent a hydrogen atom or form, together with the carbon atom-to which they are bonded, a >CO group, $R_2$ represents an isopropyl, 1-methylpropyl, tert-butyl or cyclohexylmethyl radical, $R'_2$ represents a hydrogen atom, $X_2$ and $Y_2$ each represent a hydrogen atom or form, together with the carbon atom to which they are bonded, a >C=O group, $R_3$ represents a methyl or ethyl radical substituted by a hydroxyl, methoxy, mercapto or methylthio radical, $R'_3$ represents a hydrogen atom, and R represents a hydrogen atom or an alkyl radical containing 1 to 4 carbon atoms.

The products of general formula (I) in which $R_1$ represents a 2-mercaptoethyl or 1-amino-2-mercaptoethyl radical, $X_1$ and $Y_1$ each represent a hydrogen atom or form, together with the carbon atom to which they are bonded, a >CO group, $R_2$ represents an isopropyl radical, $X_2$ and $Y_2$ each represent a hydrogen atom or form, together with the carbon atom to which they are bonded, a >C=O group, $R'_2$ represents a hydrogen atom, $R_3$ represents a 2-(methylthio) ethyl or 2-(methylsulphinyl)ethyl radical, $R'_3$ represents a hydrogen atom and R represents a hydrogen atom are very particularly advantageous.

The present invention also relates to the stereoisomeric forms of the products of general formula (I). The amino acid residues represented by $R_1C(X_1)(Y_1)$, $R_2CH(NR'_2)$ [$C(X_2)(Y_2)$] and $R_3CH(NR'_3)CO$—OH preferably have the configuration of the natural amino acids.

The present invention also relates to the inorganic or organic salts, and the esters, of the products of general formula (I).

According to the invention, the new products of general formula (I) can be obtained by synthesis on a solid phase using a "9-fluorenylmethoxycarbonyl (FMOC)" synthesis strategy. In this case, the thiol groups are protected with trityl or acetamidomethyl groups, the amine functional groups with Boc (t-butoxycarbonyl) groups and the acid functional groups in the t-butyl ester form, the alcohol functional groups with t-butyl groups and the amide and imidazole functional groups with trityl groups. The synthesis can be carried out on a resin confined in 3 cm$^3$ solid-phase extraction syringes made of high density polyethylene equipped with Teflon filters. The syringes are mounted on a two-way Teflon valve and are closed by a disposable high density polyethylene finned plug. Agitation of the syringes is carried out on a rotary device for haemolysis tubes. The washing and filtering operations are carried out on a solid-phase extraction work station.

The syntheses are then carried out on 50 μmol of resin. The couplings of the amino acids are carried out by treating the resin for 1 hour with 250 μmol of the suitably protected amino acid in the presence of 250 μmol of 2-(1H-benzotriazole-1-yl)-1,1,3,3-tetramethyluronimum, tetramethyluronium, hexafluorophosphate (BTUH), 250 ∞mol of N-hydoxybenzotriazole and 750 μmol of diisopropylethylamine in 1.2 cm$^3$ of an N-methyl-2-pyrrolidone (NMP)/dimethylformamide (1/1 by volume) mixture. Deprotection of the FMOC group is carried out with 3 successive treatments of the resin for 2 times 1 minute and then 20 minutes with 2 cm$^3$ of piperidine as a 2% (v/v) solution in NMP.

For example, Cys-(NMe)Val-[cis-3-phenyl-DL-prolyl]-Met can be prepared in the following way:

50 μmol of Fmoc-Met-chlorotrityl resin are successively subjected to the following treatments:

deprotection of the FMOC group, washing with 5 times 2 cm$^3$ of NMP, coupling of FMOC-cis-3-phenyl-DL-proline, washing with 5 times 2 cm$^3$ of NMP, deprotection of the FMOC group, washing with 5 times 2 cm$^3$ of NMP, coupling of FMOC-N-methylvaline, washing with 5 times 2 cm$^3$ of NMP, deprotection of the FMOC group, washing with 5 times 2 cm$^3$ of NMP, coupling of FMOC-cysteine(S-trityl), washing with 5 times 2 cm$^3$ of NMP, deprotection of the FMOC group, washing with 5 times 2 cm$^3$ of NMP.

On completion of the synthesis, the products are separated by treatment of-the resin with 10 cm$^3$ of a trifluoroacetic acid/phenol/ethanedithiol/thioanisole/-water (40/3/1/2/2 by volume) mixture for 1 hour 30 minutes. The resin is then removed by filtration. The filtrate is concentrated under reduced pressure by means of a centrifugal evaporator (RC10-10 Jouan) equipped with a vane pump and with a trap at −90° C. for 1.5 hours, the temperature of the evaporation chamber being maintained at 50° C. The final volume of the concentrate is approximately 1 cm$^3$. The product is then precipitated by addition of 15 cm$^3$ of a mixture of methyl tert-butyl ether and petroleum ether (2/1 by volume) and it is then collected by centrifuging. The pellet is then dissolved in 1 cm$^3$ of trifluoroacetic acid, precipitated by addition of 15 cm$^3$ of methyl tert-butyl ether and then washed with 15 cm$^3$ of methyl tert-butyl ether. The product is then dried under reduced pressure (3.5 kPa). The product is finally purified by high performance liquid chromatography (HPLC) on a $C_{18}$ 100 Å column (250×10 mm, BioRad) eluted with a gradient of acetonitrile containing 0.07% of trifluoroacetic acid (by volume) in water containing 0.07% of trifluoroacetic acid (by volume) at a flow rate of 6 cm$^3$/min and then lyophilized. The products obtained are characterized by their mass spectra (electrospray).

Introduction of the FMOC protective group onto an amino acid is carried out by reaction of the amino acid with 9-fluorenylmethyl chloroformate (FMOC-chloride) in the presence of a base.

The FMOC-Met-chlorotrityl resin can be obtained by reaction of 250 μmol of chlorotrityl chloride resin (Novabiochem®) with 1 mmol of FMOC-Methionine in 2 cm$^3$ of dichloromethane and 0.5 cm$^3$ of diisopropylethylamine for 30 minutes. After addition of 2 cm$^3$ of methanol, the reaction is continued for a further 30 minutes. The resin is then washed with 5 times 4 cm$^3$ of dichloromethane and then dried.

The cis- and trans-phenylprolines, in the racemic form, can be obtained under the conditions described by R. Sarges and J. R. Tretter, J. Org. Chem., 39, 1710 (1974).

The inhibitory activity with respect to farnesyl transferase and to farnesylation of the Ras protein may be demonstrated in the following test:

Farnesyl transferase activity is determined by the quantity of [$^3$H]farnesyl transferred from [$^3$H]farnesyl pyrophosphate [[$^3$H]FPP) to the p21 H-ras protein. The standard reaction mixture is composed, for a final volume of 60 μl, of 50 mM Tris-HCl, 5 mM MgCl$_2$, 5 mM dithiotreitol, 0.2% octyl β-D-glucopyranoside, 200 picomol p21 H-ras, 4.5 picomol [³H]FPP (activity 61000 dpm/picomol).

Reaction is initiated by adding approximately 5 ng of human farnesyl transferase purified from THP1 cell cultures. After incubation for 20 minutes at 37° C. in a microtitration plate containing 96 1-cm³ wells per plate (Titer Plate®, Beckman), the reaction is stopped by adding 0.4 cm³ of 0.1% SDS in methanol at 0° C. The mixture is then treated with 0.4 cm³ of 30% trichloroacetic acid® (TCA) in methanol. The plates are left in ice for 1 hour. The precipitated contents are then retained on Filtermat®, Pharmacia) glass fibres membranes with the filtration unit (Combi Cell Harvester®, Skatron), and rinsed with 6% trichloroacetic acid in distilled water. The membranes are dried in a microwave oven, then impregnated with scintillation medium by melting Meltilex® (Pharmacia) under hot air, and lastly counted in cpm in a β-Plate® counter (LKB). Each test is repeated 3 times.

The unit of activity is defined as 1 picomol of [³H]FPP transferred to p21 H-ras in 20 minutes.

The percentage inhibition values are obtained by comparison of the tests with and without inhibitor after deduction of blanks, the $IC_{50}$ values being measured on the basis of the inhibitions obtained with 9 different concentrations using Enzfitter® or Grafit® software.

The results obtained are collated in Table I.

TABLE I

| Product | Inhibitory activity $IC_{50}$ |
|---|---|
| Cys-(N-Me)Val-[cis-3-phenyl-DL-prolyl]-Met | $1.55 \times 10^{-8}$ M |
| Cys-(N-Me)Val-[trans-3-phenyl-DL-prolyl]-Met | $9.2 \times 10^{-7}$ M |

The new peptides of general formula (I) can be in the form of non-toxic and pharmaceutically acceptable salts. These non-toxic salts comprise the salts with inorganic acids (hydrochloric, sulphuric, hydrobromic, phosphoric and nitric acids) or with organic acids (acetic, propionic, succinic, maleic, hydroxymaleic, benzoic, fumaric, methanesulphonic, trifluoroacetic or oxalic acid), or with inorganic bases (sodium hydroxide, potassium hydroxide, lithium hydroxide, calcium hydroxide) or organic bases (tertiary amines such as triethylamine, piperidine, benzylamine), depending on the nature of the constituent amino acids of the peptide of general formula (I).

The new peptides according to the invention, which inhibit farnesyl transferase and farnesylation of the Ras protein, are notable anticancer agents which are active as regards both solid and non-solid tumours.

The present invention also relates to pharmaceutical compositions containing at least one peptide of general formula (I), in combination with one or more pharmaceutically acceptable diluents or adjuvants, which may be either inert or physiologically active.

These compositions may be administered orally, parenterally or rectally.

The compositions for-oral administration comprise tablets, pills, powders or granules. In these compositions, the active product according to the invention is mixed with one or more inert diluents such as sucrose, lactose or starch. These compositions can comprise substances other than diluents, for example lubricants such as magnesium stearate.

As liquid compositions for oral administration, solutions, suspensions, syrups, elixirs and pharmaceutically acceptable emulsions, containing inert diluents such as water or liquid paraffin, may be used. These compositions can also comprise substances other than diluents, for example wetting, sweetening or flavouring products.

The compositions according to the invention for parenteral administration can be sterile solutions, aqueous or non-aqueous, suspensions or emulsions. As solvent or vehicle, propylene glycol, a polyethylene glycol, vegetable oils, especially olive oil, or injectable organic esters, for example ethyl oleate, may be employed. These compositions can also contain adjuvants, especially wetting, emulsifying and dispersing agents. The sterilization may be carried out in several ways, for example using a bacteriological filter, by incorporating sterilizing agents in the composition or by heating. They may also be prepared in the form of sterile solid compositions which can be dissolved at the time of use in sterile water or any other sterile injectable medium.

The compositions for rectal administration are suppositories which can contain, besides the active product, excipients such as cocoa butter.

The compositions according to the invention are especially useful in human therapy in the treatment of cancers of various origins.

In human therapy, the doses depend on the effect sought, the period of treatment and factors specific to the subject to be treated.

Generally, in man, the doses are between 0.1 and 20 mg/kg per day via the intraperitoneal route.

I claim:

1. A compound of formula:

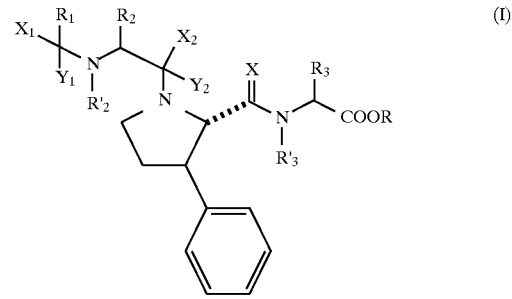

in which:

$R_1$ represents a radical of formula $Y-S-A_1-$;

Y represents a hydrogen atom, an amino acid residue, a fatty acid residue, an alkyl radical, an alkoxycarbonyl radical or a $R_4-S-$ radical;

$R_4$ represents an alkyl radical of 1 to 6 carbon atoms, optionally substituted by a phenyl radical, or a radical of formula

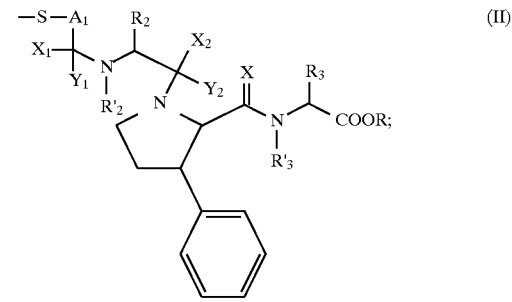

$A_1$ represents a straight or branched alkylene radical of 1 to 4 carbon atoms, optionally substituted at the position α to the $>C(X_1)(Y_1)$ group by an amino radical, an alkylamino radical of 1 to 4 carbon atoms, an alkanoylamino radical of 1 to 4 carbon atoms or an alkoxycarbonylamino radical in which the alkyl part is of 1 to 4 carbon atoms;

$X_1$ and $Y_1$ each represent a hydrogen atom or form, together with the carbon atom to which they are bonded, a >C=O group;

$R_2$ represents a straight or branched alkyl radical of 1 to 4 carbon atoms, optionally substituted by a cyclohexyl radical;

$R'_2$ represents a hydrogen atom or a straight or branched alkyl radical of 1 to 6 carbon atoms;

$X_2$ and $Y_2$ each represent a hydrogen atom or form, together with the carbon atom to which they are bonded, a >C=O group;

$R_3$ represents a straight or branched containing alkyl radical of 1 to 4 carbon atoms, optionally substituted by a hydroxyl radical, an alkoxy radical of 1 to 4 carbon atoms, a mercapto radical, an alkylthio radical of 1 to 4 carbon atoms, an alkylsulphinyl radical of 1 to 4 carbon atoms or an alkylsulphonyl radical of 1 to 4 carbon atoms, wherein, when $R_3$ represents a hydroxyalkyl radical, $R_3$ can form a lactone with the carboxyl radical at the α position;

$R'_3$ represents a hydrogen atom or a straight or branched alkyl radical of 1 to 6 carbon atoms;

X represents an oxygen or sulphur atom; and

R represents a hydrogen atom or an alkyl radical, optionally substituted by an alkoxy radical of 1 to 4 carbon atoms, an alkylthio radical of 1 to 4 carbon atoms, an alkylsulphinyl radical of 1 to 4 carbon atoms, an alkylsulphonyl radical of 1 to 4 carbon atoms, a phenoxy radical, a phenylthio radical, a phenylsulphinyl radical, a phenylsulphonyl radical, an alkylamino radical of 1 to 4 carbon atoms or a dialkylamino radical in which each alkyl group is of 1 to 4 carbon atoms, or a phenyl radical, optionally substituted by at least one atom or radical, independently selected from the group consisting of a halogen atom, an alkyl radical of 1 to 4 carbon atoms, an alkoxy radical of 1 to 4 carbon atoms, an alkylthio radical of 1 to 4 carbon atoms, and alkanoyl radical of 1 to 4 carbon atoms; or a pharmaceutically acceptable salt thereof.

2. The compound according to claim 1, in which $R_1$ represents a radical of formula Y—S—$A_1$—;

Y represents a hydrogen atom, a lysine residue, or a fatty acid residue containing up to 20 carbon atoms;

$A_1$ represents an ethylene or propylene radical optionally substituted by an amino radical;

$X_1$ and $Y_1$ each represent a hydrogen atom or form, together with the carbon atom to which they are bonded, a >C=O group;

$R_2$ represents an isopropyl radical, a 1-methylpropyl radical, a teit-butyl radical or a cyclohexylmethyl radical;

$R'_2$ represents a hydrogen atom or a methyl radical;

$X_2$ and $Y_2$ each represent a hydrogen atom or form, together with the carbon atom to which they are bonded, a >C=O group;

$R_3$ represents a methyl or ethyl radical substituted by a hydroxyl, methoxy, mercapto, methylthio, methylsulphinyl or methylsulphonyl radical;

$R'_3$ represents a hydrogen atom or a methyl radical;

X represents an oxygen atom; and

R represents a hydrogen atom or an alkyl radical containing 1 to 4 carbon atoms, optionally substituted by an alkoxy radical, or a phenyl radical; or a pharmaceutically acceptable salt thereof.

3. The compound according to claim 1, in which $R_1$ represents a radical of formula Y—S—$A_1$—;

Y represents a hydrogen atom;

$A_1$ represents an ethylene or propylene radical optionally substituted by an amino radical;

$X_1$ and $Y_1$ each represent a hydrogen atom or form, together with the carbon atom to which they are bonded, a >CO group;

$R_2$ represents a isopropyl radical, a 1-methylpropyl radical, a tert-butyl radical or a cyclohexylmethyl radical;

$R'_2$ represents a hydrogen atom;

$X_2$ and $Y_2$ each represent a hydrogen atom or form, together with the carbon atom to which they are bonded, a >C=O group;

$R_3$ represents a methyl or ethyl radical substituted by a hydroxyl, methoxy, mercapto or methylthio radical;

$R'_3$ represents a hydrogen atom; and

R represents a hydrogen atom or an alkyl radical containing 1 to 4 carbon atoms; or a pharmaceutically acceptable salt thereof.

4. The compound according to claim 1, in which $R_1$ represents a 2-mercaptoethyl or 1-amino-2-mercaptoethyl radical;

$X_1$ and $Y_1$ each represent a hydrogen atom or form, together with the carbon atom to which they are bonded, a >CO group;

$R_2$ represents an isopropyl radical;

$X_2$ and $Y_2$ each represent a hydrogen atom or form, together with the carbon atom to which they are bonded, a >C=O group;

$R'_2$ represents a hydrogen atom;

$R_3$ represents a 2-(methylthio)ethyl or 2-(methylsulphinyl)ethyl radical;

$R'_3$ represents a hydrogen atom; and

R represents a hydrogen atom; or a pharmaceutically acceptable salt thereof.

5. The compound according to claim 1 wherein $R_1C(X_1)(Y_1)$, $R_2CH(NR'_2)[C(X_1)(Y_2)]$ and $R_3CH(NR'_3)COOH$ moieties represent amino acid residues which are independently of the L or D configuration.

6. The compound according to claim 5 wherein each amino acid residue is of the D configuration.

7. The compound according to claim 5 wherein each amino acid residue is of the L configuration.

8. A compound selected from the group consisting of
Cys-(N-Me)Val-[cis-3-phenyl-D-prolyl]-Met;
Cys-(N-Me)Val-[cis-3-phenyl-L-prolyl]-Met;
Cys-(N-Me)Val-[trans-3-phenyl-D-prolyl]-Met; and
Cys-(N-Me)Val-[trans-3-phenyl-L-prolyl]-Met.

9. A mixture of diastereomers comprising
Cys-(N-Me)Val-[cis-3-phenyl-D-prolyl]-Met and
Cys-(N-Me)Val-[cis-3-phenyl-L-prolyl]-Met.

10. A mixture of diastereomers comprising
Cys-(N-Me)Val-[trans-3-phenyl-D-prolyl]-Met and
Cys-(N-Me)Val-[trans -3-phenyl-L-prolyl]-Met.

11. A pharmaceutical composition comprising a pharmaceutically acceptable amount of a compound according to claim 1 and an inert or physiologically active pharmaceutically acceptable diluent or adjuvant.

12. A method of inhibiting farnesyl transferase in a patient, comprising administering to a patient a therapeutically effective dose of a compound according to claim 1 or a pharmaceutically acceptable salt thereof.

13. A method of inhibiting farnesyl transferase, comprising contacting a farnesyl transferase inhibitory amount of a compound according to claim 1, or a salt thereof with a composition containing farnesyl transferase.

14. A method for treating cancer, caused by mutated ras protein, in a patient comprising administering to the patient a therapeutically effective dose of a compound according to claim 1, or a pharmaceutically acceptable salt thereof.

15. A method for cancer therapy, wherein the cancer is associated with farnesyl transferase activity, comprising administering to a patient in need of such therapy a therapeutically effective amount of a compound according to claim 1, or a pharmaceutically acceptable salt thereof.

16. A method for treating cancer in a patient, comprising administering to the patient a therapeutically effective dose of a compound according to claim 1, or a pharmaceutically acceptable salt thereof.

17. The method according to claim 16 wherein the administering is oral, parenteral or rectal.

18. The method according to claim 16 wherein the therapeutically effective dose is between 0.1 and 20 mg/kg per day.

* * * * *